United States Patent [19]

Geirnaert

[11] Patent Number: 4,560,660
[45] Date of Patent: Dec. 24, 1985

[54] FIXATION SUPPORT FOR MICROORGANISMS

[75] Inventor: Gilles Geirnaert, Saint-Palais-sur-Mer, France

[73] Assignee: Argiles & Mineraux AGS-BMP, Montguyon, France

[21] Appl. No.: 485,417

[22] Filed: Apr. 15, 1983

[30] Foreign Application Priority Data

Apr. 27, 1982 [FR] France .................................. 82 07205
Sep. 21, 1982 [FR] France .................................. 82 15845

[51] Int. Cl.$^4$ ....................... C12N 11/14; C04B 35/04
[52] U.S. Cl. ..................................... 435/176; 501/118; 501/121; 501/128
[58] Field of Search ................ 435/176; 501/121, 118, 501/128

[56] References Cited

U.S. PATENT DOCUMENTS 3,950,175  4/1976  Lachman et al. .................... 501/118
4,149,936  4/1979  Messing et al. ...................... 435/176
4,448,884  5/1984  Henderson ........................... 435/176

*Primary Examiner*—Sam Rosen
*Attorney, Agent, or Firm*—Browdy and Neimark

[57] ABSTRACT

A ceramic support for the fixation of microorganisms thereto consists of a silico-aluminate having 5–25% magnesia and an average granulometry of 5–300 microns, with the coarsest grains being no more than two times the diameter of the finest grains, and preferably less than 1.5 times the diameter of the smallest grains. This support, which is suitably obtained by calcining a mixture of kaolinic clay and talc or magnesium carbonate and containing no more than 50% cordierite, then grinding and sintering to the desired granulometric distribution, is particularly desirable in the fixing thereto of hybridomas to produce monoclonal antibodies, or biological catalysts.

18 Claims, 4 Drawing Figures

SUPPORT A

TIME (HOURS)

FIXATION SUPPORT FOR MICROORGANISMS

FIELD OF THE INVENTION

This invention relates to the field of inorganic matter used as insoluble supports for the fixing of enzymes and/or microorganisms such as mushrooms, bacteria, yeasts, viruses or any other mono- or polycellular living matter. More specifically, it relates to a new ceramic-type support, containing at least 50% cordierite, with very special characteristics.

BACKGROUND OF THE INVENTION

For a long time it has been known how to prepare and use supports, especially those made of porous inorganic matter, to fix microbial populations such as bacteria, yeasts, enzymes or others by adsorption or other phenomenon, and thus to constitute biological catalysts usable for multiple applications in the most diverse industrial and agricultural fields.

In other supports of fritted glass materials, crystalline materials such as spinel-zircon or cordierite have been recommended. It has been clearly specified that these products should have, with a rate of least 70%, average diameters of well delimited pores, such as 0.8 to 220 microns for a bacteria population and 1 to 140 microns for yeast cells; in French Pat. No. 78.26415 and U.S. Pat. No. 4,149,937, the declared granulometry for the supports was specified as about 0.7 to 1 mm.

It has also been found that in the case of some inorganic materials, the amount of biomass fixed per surface unit of the material and the stabilization in time of the biocatalyst obtained were not necessarily a function of the porosity of the product nor of the need to have at its disposal an average pore diameter at least equal to, and preferably several times greater than, a diameter of the microorganism to be fixed. The effectiveness of the catalyst can actually be profoundly affected by phenomena of restriction of accessibility, mechanical or physical, for the organisms. For example, in supports with great porosity, the enzymes which line the pore walls show very reduced activity specifically because of the composition of a diffusion boundary layer at the surface of the solid support, this layer constituting a barrier which slows down the reactions caused by the biomass.

SUMMARY OF THE INVENTION

The object of the invention is to offer a support which, irrespective of the porosity requirements, not only facilitates significant activity in a reactive medium but also exhibits greater stability over long periods of time, particularly by yielding conversion rates, during its use as a biocatalyst, which are constant for as long as one or more months.

DESCRIPTION OF PREFERRED EMBODIMENTS

Figure 1:
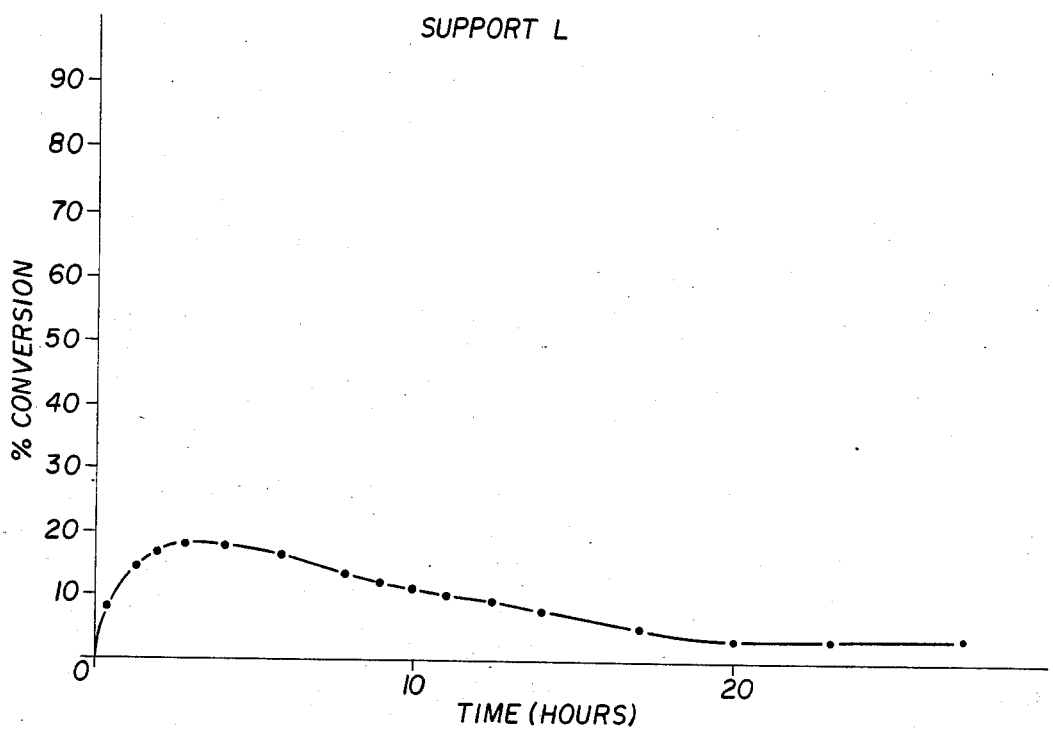
FIG. 1 is a graphical illustration showing a curve conversion against time for support L.

The new support according to the invention consists essentially of a silicoaluminate having well-determined magnesia contents of preferably between 5% and 25% (by weight), and having an average granulometry of between 5 and 300 microns, with the diameter of the coarsest grains being at the maximum two times that of the smallest, and advantageously being less than one and a half times.

From the crystallographic point of view, the support is of the synthetic cordierite type in which the iron content, expressed as $Fe_2O_3$, is less than 2%. Although it can be obtained by other methods or variants, this material is advantageously prepared by mixing kaolinic clay with talc or magnesium carbonate, then effecting calcination at 1000°–1400° C. and then fine grinding the resulting material to obtain the desired granulometry range. For example, if talc is used, the amount will advantageously be close to 30% by weight (for 70% clay) while it will be on the order of 20% for magnesium carbonate. Increasing the speed of calcination and reducing the temperature level of the latter can also be done by incorporating into the cordierite paste a small percentage, for example, preferably 5% to 10%, of finely ground synthetic cordierite, of, for example, ARTAL 23, which acts as a crystal nucleus.

Among the numerous applications of the supports according to the invention, two nonlimiting examples are described below in detail, one illustrating the bacteria fixation for the production of proteins and the other illustrating the formation of macromolecules, for example antibodies, secreted by living organisms.

EXAMPLE 1

This example relates to making continuous a bioreactor for the production of tryptophan by fixing Echerichia coli cells on a support using indole as substrate. Comparisons with other supports that do not satisfy the critical parameters of the invention have also been made.

(a) Supports used. The support of the invention, hereafter referred to as "A", was prepared by mixing 70 parts kaolinic clay ($KR_2$) and 30 parts talc (2 C), then calcining at a temperature of 1350° C. and grinding-sifting so as to retain only the fine particles and grains that exhibit a granulometry range entirely between 100 and 200 microns. Its chemical composition was as follows: $SiO_2$: 53.7; $Al_2O_3$:30.8; $Fe_2O_3$:1.6; $TiO_2$:1.1; $K_2O+Na_2O$:0.6; $MgO$:9.6. As for the mineralogical structure, it corresponded roughly to 80% cordierite, 8% mullite and 12% glass.

By way of comparison, the same experiments have also been made with two silico-aluminate type supports of compositions rather close to those of product A but, containing very little magnesia, namely:

Support L-$SiO_2$:54.3; $Al_2O_3$:41.3; $FeO_3$:1.9; $TiO_2$:1.4; $K_2O+Na_2O$:0.7; $CaO+MgO$:0.4

Support X-$SiO_2$:53.6; $Al_2O_3$:44.2; $Fe_2O_3$:0.9; $TiO_2$:0.8; $K_2O+Na_2O$:0.3; $CaO+MgO$:0.2.

On the crystallographic level, these two supports contain approximately equivalent amounts of mullite, cristobalite and glass. Further, about 70% of the pores of these ceramic compositions had an average diameter between 1 and 200 microns, approximating parameters disclosed in the previously mentioned French patent.

(b) Production of tryptophan. Echerichia coli bacteria, which exhibited a high tryptophanase activity with a concentration of 0.3 g/l of tryptophan as inducer in the fermentation medium were used to start. The bacteria were used in suspension to test the enzymatic system for conversion of indole into tryptophan in a medium with the following composition: indole $10^{-2}$ mole; sodium pyruvate: 0.5 mole; ammonium acetate: 0.6 mole; pyridoxal phosphate: $10^{-3}$ mole; ethanol: 10%. The pH was about 9 and the temperature about 37° C. Different supports wer tested in a fixed bed reactor by fixing by adsorption the bacteria for several hours by circulation of the bacteria suspension at a flow of 30 ml/h in a 0.1 M (pH 7) phosphate buffer. A washing was performed with this phosphate buffer to eliminate the excess bacteria until obtaining a zero optical diffraction at output.

The column being ready, the substrate was introduced under said conditions, and the enzymatic kinematics was followed by measurement, as a function of the time of the concentration of the tryptophan and the indole. Then the curves were drawn giving the rates of production of tryptophan (in % by weight) on the x-axis as a function of time.

Figure 2:
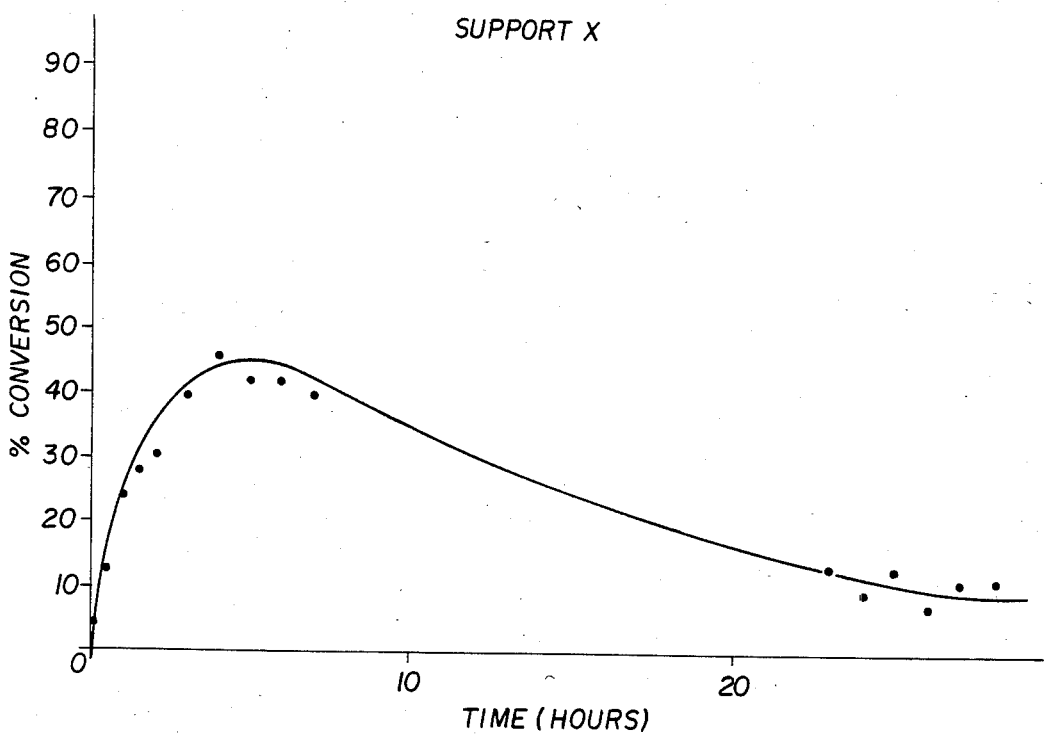
FIG. 2 is a graphical illustration showing a curve conversion against time for support X.
Figure 3:
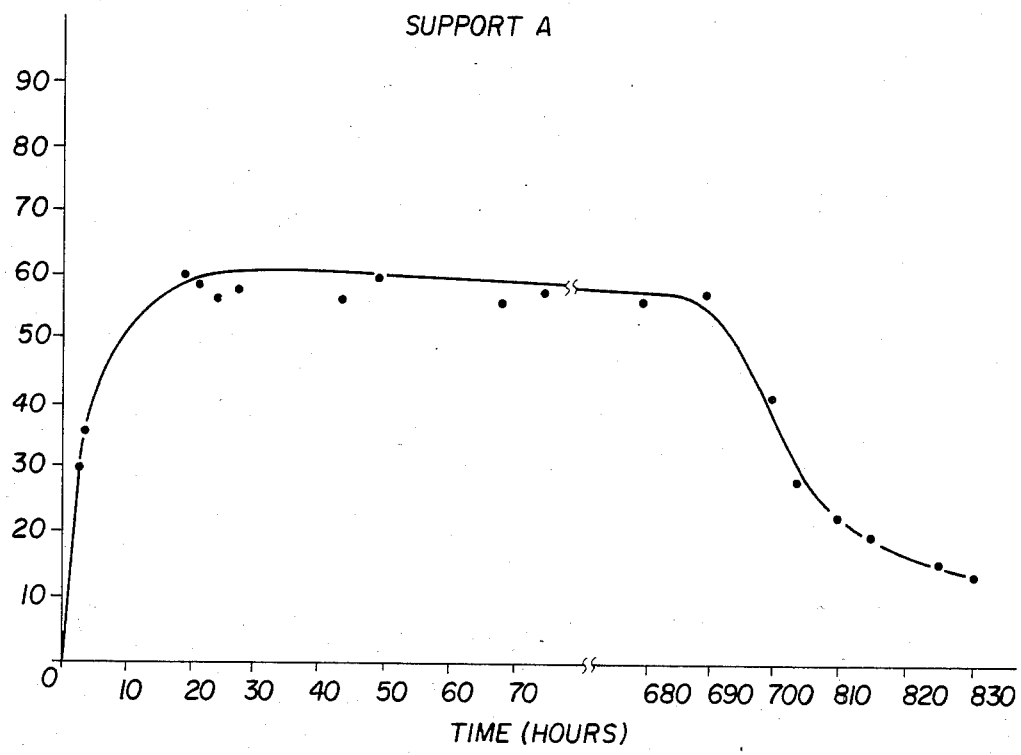
FIG. 3 is a graphical illustration showing a curve conversion against time for support A.

As can be seen in the drawings of the accompanying FIGS. 1 to 3, support X gives a bioconversion yield of about 43%, but it lasts only 3 to 4 hours. In the case of support L, the maximum yield is very low, on the order of 20% for a rather short stationary state of 2 to 5 hours. On the other hand, in using support A according to the invention, very advantageous results were obtained: actually the rate of conversion remained virtually constant, at about 60% for a period of one month without the column of bacteria needing to be recharged and without the presence of indole being found at the output of the reactor.

Thus, the supports according to the invention makes it possible to carry out the immobilization of whole bacteria and to obtain biological catalysts that allow the making of various products in continuous processes, with yields compatible with the economic constraints of the industry.

EXAMPLE 2

This example illustrates another important case for using the supports according to the invention, especially for the fixing of monocellular organisms such as, for example, trypanosomes or Leishmanias or, even better, for the fixing of hybridomas to produce monoclonal antibodies which, as is known, are used particularly in the production of serums.

The fragility and the diffusion constraints of hybridoma cells which result from the fusion of lymphocytes and myelomatous cells and makes possible the preparation of monoclonal antibodies very valuable in human immunotherapy (see, for example, the magazine "Pour la Science" November 1981 p. 38–39). The culture of these cells can be done in various ways for the growth phases, then for production of antibodies, for example by intraperitoneal injection of hybridomas into the abdominal cavity of a mouse or by batch culture on microballs of a fluidized bed support.

It has now been found that the processes for fractioning and purifying biological molecules could be appreciably simplified as the result of the use, as cell supports, of inorganic granular materials according to the invention. Actually, as a result of work done in collaboration with the Institut de Technologie des Surfaces Actives de Compiegne (France), a technique for fixing hybridomas and monoclonal antibodies by using fixed bed support columns according to the invention which function continuously was able to be developed. This technique exhibits numerous advantages such as, in particular: the separation of the culture medium, simpler than in the standard cases; the greatest ease of maintaining the sterility of the medium; and, of course, the continuous production of monoclonal antibodies.

In the embodiment below, product A, whose characteristics have been enumerated above, was used as a support for fixing of cells, in a cylindrical fixed-bed reactor.

Used as material was a thermostated cylindrical reactor about 20 cm high and about 1 cm in diameter, filled with support A (20 grams) and connected by a peristaltic pump to a gas exchanger or aeration column to supply to the culture medium with a gas containing approximately: 74% nitrogen, 20% oxygen and 6% carbon dioxide gas.

Before operation, support A was washed with HCl then dried and pasteurized at 80°–90° C. in the column for two hours, with circulation at this temperature of an alkaline phosphate buffer solution giving a pH of 7.2 to 7.4.

The hybridomas were obtained by fusion of mouse lymphocytes type BALB/C with myeloma cells type $SP_2$ and the concentrate of active material was introduced into 150 ml of a known culture medium RPMI 1640 containing 10% fetal calf serum.

The active medium was then introduced into the reactor with a flow of about 1 ml/minute corresponding to a linear speed of 1.3 cm/minute. The measurements of antibodies obtained (immunoglobulines G) were made on hydrolyzed and acetylated nylon plates (with comparison of standards on different plates) then counting in a THOMA chamber and measurement of ATP (adenosine triphosphate) by luminescence.

Table 1 below shows the energy metabolism of the culture medium during the process of fixing the cells on the support used:

TABLE 1

|  | At the input of the culture medium | At the output of the culture medium |
|---|---|---|
| Concentration of cells $10^5$/ml | 4.6 | 0 |
| ATP (PG/ml) | $8.6 \times 10^3$ | 0 |

The absence of cells and ATP in the medium that leaves the reactor clearly shows that all of the biomass has been fixed in this reactor, by a single pass, which was confirmed by use of an electron microscope.

Figure 4:
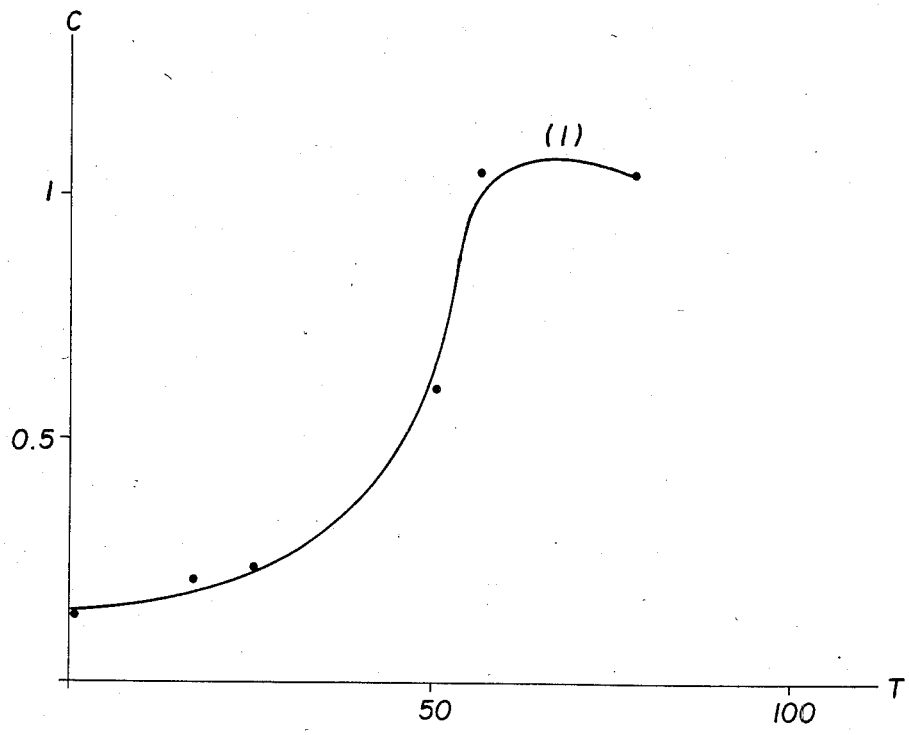
FIG. 4 shows a curve representing the concentration of immunoglobulines versus time.

Moreover, the activity of the hybridoma cells fixed on the support of the invention showed a continuous secretion of monoclonal antibodies according to a stationary phase as is clear from the curve (1) of the accompanying FIG. 4 where the x-axis T corresponds to the time in hours while the y-axis represents the concentration C of immunoglobulines (expressed in micrograms per ml).

These tests therefore demonstrated the possibility of using, in continuous phase, a fixed-bed reactor or support according to the invention, for the production of antibodies and going on from there, of various macromolecules secreted by living organisms.

I claim:

1. A ceramic product in the form of a support for the fixation of microorganisms characterized in that it consists of a silicoaluminate having contents of 5 to 25% of magnesia and whose average granulometry is between 5 and 300 microns, with such an interval that the diameter of the coarsest grains is at the maximum two times that of the smallest.

2. A ceramic support in accordance with claim 1, wherein it is obtained by calcination between 1000°–1400° C. of a mixture of kaolinic clay and talc or magnesium carbonate, then grinding and sorting to the desired granulometric distribution of the final material, containing more than 50% cordierite.

3. A ceramic support in accordance with claim 2, wherein about 70% (by weight) of kaolinic clay and 30% of talc are mixed.

4. A ceramic support in accordance with claim 2, wherein about 80% (by weight) of kaolinic clay and 20% of magnesium carbonate are mixed.

5. A ceramic support in accordance with claim 1, wherein it includes 53.7% $SiO_2$; 30.8% $Al_2O_3$; 1.6% $Fe_2O_3$; 1.1% $TiO_2$; 0.6% $Na_2O+K_2O$ and 9.6% MgO; the mineralogical structure corresponding approximately to 80% cordierite, 8% mullite and 12% glass; the granulometry being entirely between 100 and 200 microns.

6. A ceramic support in accordance with claim 2, wherein it includes 53.7% $SiO_2$; 30.8% $Al_2O_3$; 1.6% $FeO_3$; 1.1% $TiO_2$; 0.6% $Na_2O+K_2O$ and 9.6% MgO; the mineralogical structure corresponding approximately to 80% cordierite, 8% mullite and 12% glass; the granulometry being entirely between 100 and 200 microns.

7. A ceramic support in accordance with claim 3, wherein it includes 53.7% $SiO_2$; 30.8% $Al_2O_3$; 1.6% $FeO_3$; 1.1% $TiO_2$; 0.6% $Na_2O+K_2O$ and 9.6% MgO; the mineralogical structure corresponding approximately to 80% cordierite, 8% mullite and 12% glass; the granulometry being entirely between 100 and 200 microns.

8. A ceramic support in accordance with claim 4, wherein it includes 53.7% $SiO_2$; 30.8% $Al_2O_3$; 1.6% $FeO_3$; 1.1% $TiO_2$; 0.6% $Na_2O+K_2O$ and 9.6% MgO; the mineralogical structure corresponding approximately to 80% cordierite, 8% mullite and 12% glass; the granulometry being entirely between 100 and 200 microns.

9. A method of using the support of claim 1 comprising fixing a biological catalyst to said support and using the fixed catalyst for the continuous production of various substances in a bioreactor.

10. A method of using the support of claim 1 comprising fixing a hybridoma to said support and using the fixed hybridoma to produce monoclonal antibodies.

11. A ceramic support in accordance with claim 1 having fixed thereto a biological catalyst.

12. A ceramic product according to claim 1 wherein said support has fixed thereto an hybridoma.

13. A ceramic product according to claim 1 wherein the diameter of the coarsest grains is less than one and one-half times the diameter of the smallest grains.

14. A ceramic support in accordance with claim 13, wherein it is obtained by calcination between 1000°–1400° C. of a mixture of kaolinic clay and talc or magnesium carbonate, then grinding and sorting to the desired granulometric distribution of the final material, containing more than 50% cordierite.

15. A ceramic support in accordance with claim 14, wherein about 70% (by weight) of kaolinic clay and 30% of talc are mixed.

16. A ceramic support in accordance with claim 14 wherein about 80% (by weight) of kaolinic clay and 20% of magnesium carbonate are mixed.

17. A ceramic support in accordance with claim 13 having fixed thereto a biological catalyst.

18. A ceramic product according to claim 13 wherein said support has fixed thereto an hybridoma.

* * * * *